United States Patent
Pavlovich et al.

(10) Patent No.: US 9,619,730 B2
(45) Date of Patent: Apr. 11, 2017

(54) ESTIMATING MULTI-ENERGY DATA IN A RADIATION IMAGING MODALITY

(75) Inventors: Julia Pavlovich, Revere, MA (US); Ram Naidu, Newton, MA (US)

(73) Assignee: Analogic Corporation, Peabody, MA (US)

( * ) Notice: Subject to any disclaimer, the term of this patent is extended or adjusted under 35 U.S.C. 154(b) by 273 days.

(21) Appl. No.: 14/408,281

(22) PCT Filed: Jun. 29, 2012

(86) PCT No.: PCT/US2012/044853
§ 371 (c)(1),
(2), (4) Date: Dec. 15, 2014

(87) PCT Pub. No.: WO2014/003778
PCT Pub. Date: Jan. 3, 2014

(65) Prior Publication Data
US 2015/0117594 A1 Apr. 30, 2015

(51) Int. Cl.
*G01N 23/04* (2006.01)
*G06K 9/46* (2006.01)
(Continued)

(52) U.S. Cl.
CPC ............ *G06K 9/4661* (2013.01); *A61B 6/032* (2013.01); *A61B 6/4241* (2013.01); *A61B 6/482* (2013.01);
(Continued)

(58) Field of Classification Search
CPC ...... A61B 6/482; A61B 6/032; G01N 23/046; G01N 2223/419; G01N 23/087; G01N 2223/423; G01N 2223/206
See application file for complete search history.

(56) References Cited

U.S. PATENT DOCUMENTS

| | | | |
|---|---|---|---|
| 2004/0102688 A1* | 5/2004 | Walker | A61B 6/032 600/407 |
| 2005/0082491 A1* | 4/2005 | Seppi | H01L 27/14676 250/370.11 |
| 2010/0172464 A1* | 7/2010 | Pavlovich | A61B 6/032 378/9 |

FOREIGN PATENT DOCUMENTS

| | | |
|---|---|---|
| JP | 63-082628 A | 4/1988 |
| JP | 6382628 A | 4/1988 |
| WO | 2009073284 A1 | 6/2009 |

OTHER PUBLICATIONS

International Search Report cited in related application No. PCT/US2012/044853 dated Jan. 4, 2013, pp. 12.
(Continued)

*Primary Examiner* — Hoon Song
(74) *Attorney, Agent, or Firm* — Cooper Legal Group LLC (57) ABSTRACT

Multi-energy imaging is afforded with a single detector array by generating a first data set, indicative of a first radiation energy spectrum, using a first set of cells of the array, and by generating a second data set, indicative of a second radiation energy spectrum, using a second set of cells of the array (e.g., where substantially more cells are in the first set than the second). The first data set is comprised of measured data from the first set of cells and estimated data that would have been yielded from the second set of cells had the second set been configured to detect the first energy spectrum. The second data set is comprised of measured data yielded from the second set of cells and estimated data that would have been yielded from the first set of cells had the first set been configured to detect the second energy spectrum.

20 Claims, 6 Drawing Sheets

(51) Int. Cl.
*A61B 6/03* (2006.01)
*A61B 6/00* (2006.01)

(52) U.S. Cl.
CPC ......... *A61B 6/5205* (2013.01); *G01N 23/046* (2013.01); *G01N 2223/206* (2013.01); *G01N 2223/419* (2013.01); *G01N 2223/423* (2013.01)

(56) References Cited

OTHER PUBLICATIONS

Wonseok, et al., "Model-based image reconstruction for dual-energy X-ray CT with fast KVP switching", Biomedical Imaging: From Nano to Macro, 2009. ISBI '09. IEEE International Symposium on, IEEE, Piscataway, NJ, USA, Jun. 28, 2009, pp. 326-329, XP031502042, ISBN: 978-1-4244-3931-7 p. 327-p. 328.

Korean Office Action cited in Japanese Application No. 2015-520142 dated Apr. 8, 2016, 3 pgs.

EP Communication/Search Report cited in EP Application No. 12736000.6 dated Aug. 9, 2016, 5 pgs.

\* cited by examiner

ESTIMATING MULTI-ENERGY DATA IN A RADIATION IMAGING MODALITY

BACKGROUND

The present application relates to the field of imaging, and in particular to imaging modalities that produce images utilizing radiation technology (e.g., at times referred to as radiation imaging modalities or systems). It finds particular application with medical, security, and/or other applications where obtaining information about physical properties (e.g., density, effective atomic number, etc.) of an object under examination may be useful.

Computed tomography (CT) systems and other radiation imaging modalities (e.g., single-photon emission computed tomography (SPECT), mammography, digital radiography, etc.) are useful to provide information, or images, of interior aspects of an object under examination. Generally, the object is exposed to radiation photons (e.g., such as X-rays, gamma rays, etc.), and an image(s) is formed based upon the radiation absorbed and/or attenuated by the interior aspects of the object, or rather an amount of photons that is able to pass through the object. Traditionally, the image(s) that is formed from the radiation exposure is a density image or attenuation image, meaning the image is colored/shaded as a function of the respective densities of sub-objects comprised within the object under examination. For example, highly dense sub-objects absorb and/or attenuate more radiation than less dense sub-objects, and thus a sub-object having a higher density, such as a bone or metal, for example, will be shaded differently than less dense sub-objects, such as muscle or clothing.

While such imaging systems have proven successful, in some applications imaging based upon more than density may be advantageous. For example, in security applications, certain threat items can be disguised amongst clothing or other non-threat items that have similar densities to the threat items. Thus, in some applications, such as airport security, it may be useful to determine other and/or additional physical properties of the item under examination, such as, for example, effective atomic number (e.g., at times referred to as z-effective). In this way, it may be possible to discern threat items that have densities similar to non-threat items, but different atomic numbers, for example.

As early as 1992, multi-energy imaging modalities have been deployed in some environments, such as airport and military establishments, to provide additional information about an object under examination, such as an object's effective atomic number(s). These modalities have provided improved detection and/or false alarm performance when tasked to differentiate between sub-objects, relative to systems that merely differentiate sub-objects based upon density.

Multi-energy imaging modalities operate by using multiple, distinct radiation photon energy spectra to reconstruct an image(s) of an object. Such distinct radiation energy spectra can be measured using numerous techniques. For example, multi-energy measurements can be performed using energy resolving detectors (e.g., where the detectors are configured to selectively detect radiation having an energy within a first radiation energy spectrum as well as radiation having an energy within a second radiation energy spectrum), two radiation sources (e.g., respectively emitting radiation at a different energy level/spectrum), and/or by varying the voltage applied to a radiation source (e.g., such that the energy of emitted radiation varies as the applied voltage varies). It may be appreciated that the additional hardware requirements for a multi-energy imaging modality may add significant cost and/or weight to the system, often causing multi-energy imaging modalities to be significantly more expensive and/or difficult to implement than similarly designed single-energy imaging modalities.

SUMMARY

Aspects of the present application address the above matters, and others. According to one aspect, a method to estimate multi-energy data, comprising data indicative of a first radiation energy spectrum and data indicative of a second radiation energy spectrum, in a radiation imaging modality comprising a detector array comprised of a plurality of detector cells, a first set of the detector cells configured to detect the first radiation energy spectrum and a second set of the detector cells configured to detect the second radiation energy spectrum is provided. The method comprises generating a partial first data set using data yielded from the first set of detector cells, the partial first data set excluding data yielded from the second set of detector cells and generating a partial second data set using data yielded from the second set of detector cells, the partial second data set excluding data yielded from the first set of detector cells. The method also comprises estimating the data excluded from the partial first data set based upon the partial first data set to generate a complete first data set indicative of the first radiation energy spectrum and estimating the data excluded from the partial second data set based upon the partial second data set and the complete first data set to generate a complete second data set indicative of the second radiation energy spectrum.

According to another aspect, a multi-energy radiation imaging system is provided. The system comprises a radiation source configured to emit radiation and a detector array comprising a plurality of detector cells, a first set of detector cells configured to detect a first radiation energy spectrum of emitted radiation and a second set of detector cells configured to detect a second radiation energy spectrum of emitted radiation. The system also comprises a compiling component configured to generate a partial first data set using data yielded from the first set of detector cells, the partial first data set excluding data yielded from the second set of detector cells, and generate a partial second data set using data yielded from the second set of detector cells, the partial second data set excluding data yielded from the first set of detector cells. The system also comprises an estimation component configured to estimate the data excluded from the partial first data set based upon the partial first data set to generate a complete first data set indicative of the first radiation energy spectrum and estimate the data excluded from the partial second data set based upon the partial second data set and the complete first data set to generate a complete second data set indicative of the second radiation energy spectrum.

According to yet another aspect, a computer readable medium comprising computer executable instructions that when executed via a processing unit perform a method to estimate multi-energy data, comprising data indicative of a first radiation energy spectrum and data indicative of a second radiation energy spectrum, in a radiation imaging modality comprising a detector array comprised of a plurality of detector cells, a first set of the detector cells configured to detect the first radiation energy spectrum and a second set of the detector cells configured to detect the second radiation energy spectrum is provided. The method comprises generating a partial first data set using data yielded from the first set of detector cells, the partial first data set excluding data yielded from the second set of detector cells and generating a partial second data set using data yielded from the second set of detector cells, the partial second data set excluding data yielded from the first set of detector cells. The method also comprises estimating the data excluded from the partial first data set based upon the partial first data set to generate a complete first data set indicative of the first radiation energy spectrum and estimating the data excluded from the partial second data set based upon the partial second data set and the complete first data set to generate a complete second data set indicative of the second radiation energy spectrum.

FIGURES

The application is illustrated by way of example and not limitation in the figures of the accompanying drawings, in which like references indicate similar elements and in which.

DESCRIPTION

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

Among other things, one or more systems and/or techniques are described herein for estimating multi-energy projection data in a radiation imaging modality. A detector array of the radiation imaging modality comprises a first set of detector cells and a second set of detector cells. The first set (e.g., a non-filtered set) is configured to detect a first radiation energy spectrum (e.g., 80-100 keV) and the second set (e.g., a filtered set) is configured to detect a second radiation energy spectrum (e.g., 90-100 keV) to, in effect, create multi-energy data.

As will be described in more detail below, a surface area of the first set of detector cells may be (significantly) disproportionate to a surface area of the second set. For example, in one embodiment where a detector array is comprised of 24 rows of detector cells, the second set may comprise two rows of detector cells and the first set may comprise the remaining twenty-two rows of detector cells.

Typically, two substantially complete data sets (e.g., respectively comprising data acquired from all or substantially all of the detector cells of the detector array) are required to form a multi-energy image and/or to perform dual-energy decomposition. The first complete data set is indicative of the first radiation energy spectrum and the complete second data set is indicative of the second radiation energy spectrum. It may be appreciated that because the detector array is divided into two sets of detector cells (e.g., respectively configured to detect a different radiation energy spectrum), complete data sets cannot be yielded merely from the measured data. More particularly, the measured data yielded from the second set of detector cells is excluded from a complete first data set, indicative of the first radiation energy spectrum, because the measured data yielded from the second set is indicative of the second radiation energy spectrum. Likewise, measured data yielded from the first set of detector cells is excluded from a complete second data set, indicative of the second radiation energy spectrum, because the measured data yielded from the first set is indicative of the first radiation energy spectrum.

To generate the complete first data set, indicative of a first radiation energy spectrum, an estimate of the data that would have been yielded from the second set of detector cells, had the second set been configured to detect the first radiation energy spectrum, is combined with measured data yielded from the first set of detector cells. Similarly, the complete second data set, indicative of the second radiation energy spectrum, is generated by combining the measured data yielded from the second set of detector cells with an estimate of the data that would have been yielded from the first set of detector cells had the first set been configured to detect the second radiation energy spectrum. That is, the complete first data set and the complete second data set may respectively be a combination of measured data and estimated data, although the ratio of measured data to estimated data in the complete first data set may be different than the ratio of measured data to estimated data in the complete second data set. For example, a majority of the data comprised in the complete first data set may be measured data whereas the majority of data comprised in the complete second data set may be estimated data (e.g., where a greater number of rows of the detector array are configured to detect the first radiation energy spectrum than are configured to detect the second radiation energy spectrum).

Because the surface area of the first set of detector cells may be (significantly) disproportionate to (e.g., greater than) the surface area of the second set (e.g., meaning the amount of data yielded from the first set, indicative of the first radiation energy spectrum, may be disproportionate to the amount of data yielded from the second set, indicative of the second radiation energy spectrum), different techniques may be utilized to estimate measured data excluded from respective complete data sets. For example, a standard interpolation technique may be performed using merely the measured data from the first set of detector cells to estimate the data that would have been produced by the second set of detector cells if the second set had measured the first radiation energy spectrum (e.g., because the amount of data yielded from the first set of detector cells may be sufficient to perform such an interpolation). However, such a technique may not be viable for estimating the data that would have been produced by the first set of detector cells had the first set measured the second radiation energy spectrum because an insufficient amount of data may be produced by the second set of detector cells from which to perform a standard interpolation (e.g., because merely 2 out of 24 rows of detector cells are configured to measure the second radiation energy spectrum).

To estimate the data that would have been produced by the first set of the detector cells had the first set been configured to detect the second radiation energy spectrum (e.g., as opposed to the first radiation energy spectrum), both the complete first data set (e.g., indicative of the first radiation energy spectrum) and measured data yielded from the second set of detector cells (e.g., indicative of the second radiation energy spectrum) may be utilized. Thus, data indicative of the first radiation energy spectrum and data indicative of the second radiation energy spectrum may be used to estimate the data that would have been produced by the first set of the detector cells had the first set been configured to detect the second radiation energy spectrum. In this manner, both first and second energy spectra may be (cost effectively) measured with merely a single detector array.

Figure 1:
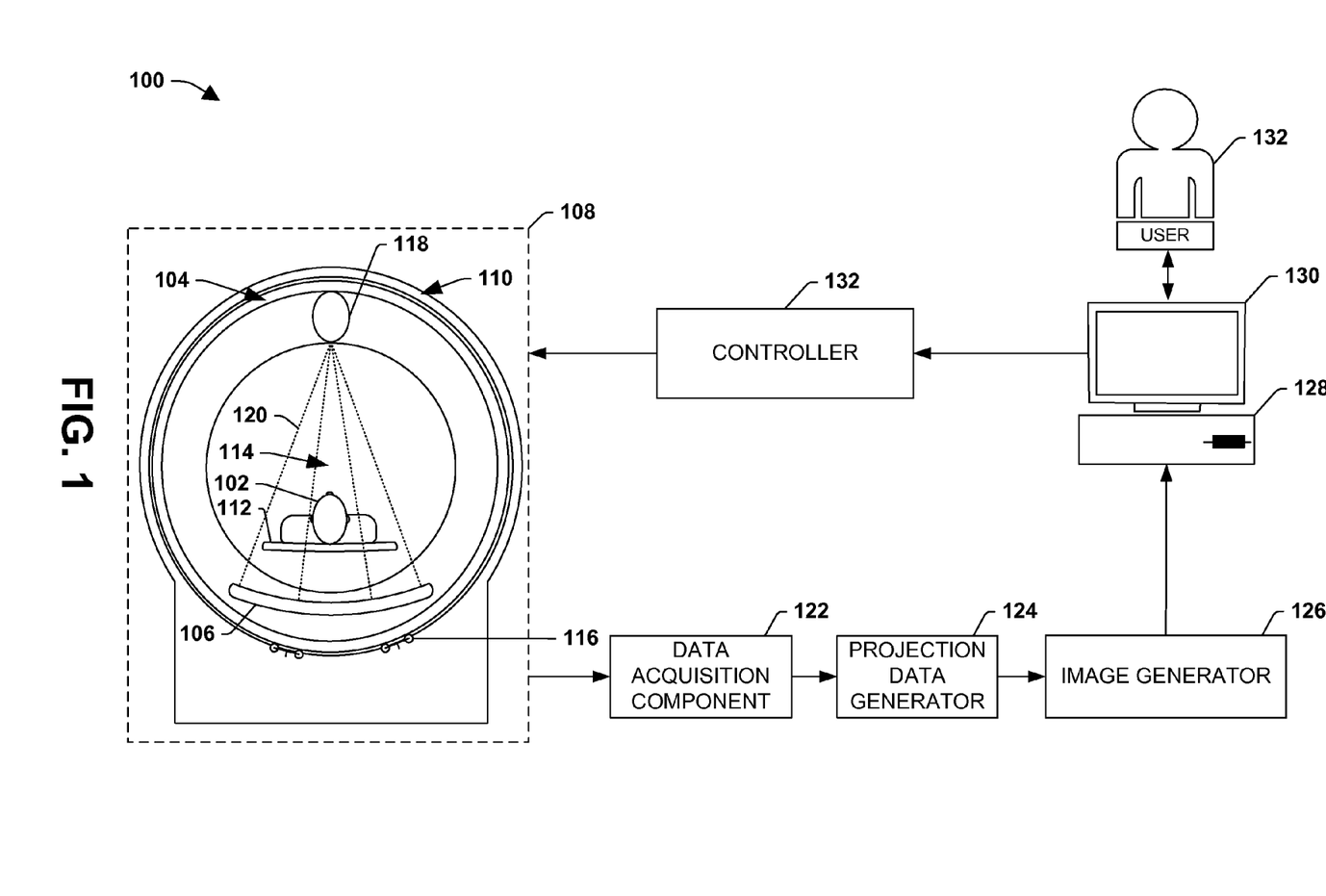
FIG. 1 is a schematic block diagram illustrating an example examination environment for examining an object.

FIG. 1 is an illustration of an example environment 100 comprising a computed tomography (CT) system that may be configured to estimate multi-energy projection data (e.g., comprising data indicative of a first radiation energy spectrum and data indicative of a second radiation energy spectrum) and to generate multi-energy images therefrom. It may be appreciated that while the example environment 100 describes a CT system configured to generate multi-energy two-dimensional, three-dimensional, four-dimensional, etc. images of the object 102 under examination, other radiation imaging modalities are also contemplated. For example, line systems and/or projection systems may be utilized to generate multi-energy two-dimensional images of an object. Moreover, the arrangement of components and/or the types of components included in the example environment 100 are merely provided as examples. By way of example, in another embodiment, the data acquisition component 122 may be comprised within the detector array 106.

In the example environment 100, an examination unit 108 of the CT system is configured to examine one or more objects 102. The examination unit 108 can comprise a rotating gantry 104 and a (stationary) support structure 110 (e.g., which may encase and/or surround at least a portion of the rotating gantry 104 (e.g., as illustrated with an outer, stationary ring, surrounding an outside edge of an inner, rotating ring)). During an examination of the object(s) 102, the object(s) 102 can be placed on a support article 112, such as a bed or conveyor belt, for example, that is selectively positioned in an examination region 114 (e.g., a hollow bore in the rotating gantry 104), and the rotating gantry 104 can be rotated and/or supported about the object(s) 102 by a rotator 116, such as a motor, drive shaft, chain, roller truck, etc.

The rotating gantry 104 may surround a portion of the examination region 114 and may comprise one or more radiation sources 118 (e.g., ionizing radiation sources such as an X-ray source and/or a gamma source) and a detector array 106 that is mounted on a substantially diametrically opposite side of the rotating gantry 104 relative to the radiation source(s) 118. As will be described in more detail below, the detector array is comprised of a plurality of detector cells configured to detect radiation, with a first set of the detector cells configured to detect a first radiation energy spectrum and a second set of detector cells configured to detect a second radiation energy spectrum. The first and second radiation energy spectra may be overlapping or non-overlapping. For example, in one embodiment, the first set of detector cells may be configured to detect radiation with an energy between 80 keV and 100 keV and the second set of detector cells may be configured to detect radiation with an energy between 90 keV and 100 keV. In another embodiment, the first set may be configured to detect radiation with an energy between 75-85 keV and the second set may be configured to detect radiation with an energy between 90-100 keV. Typically, the radiation source(s) 118 is configured to emit radiation in an energy range that spans the detectable radiation energy spectra of the first and second sets of detector cells. Thus, in the second example, the radiation source(s) 118 may be configured to emit radiation in the range of approximate 75 keV to approximately 100 keV, for example.

During an examination of the object(s) 102, the radiation source(s) 118 emits fan, cone, wedge, and/or other shaped radiation 120 configurations from a focal spot(s) of the radiation source(s) 118 (e.g., a region within the radiation source(s) 118 from which radiation 120 emanates) into the examination region 114. It may be appreciated that such radiation 120 may be emitted substantially continuously and/or may be emitted intermittently (e.g., a brief pulse of radiation is emitted followed by a resting period during which the radiation source 118 is not activated).

As the emitted radiation 120 traverses the object(s) 102, the radiation 120 may be attenuated differently by different aspects of the object(s) 102. Because different aspects attenuate different percentages of the radiation 120, an image(s) may be generated based upon the attenuation, or variations in the number of photons that are detected by the detector array 106 or by respective detector cells. For example, more dense aspects of the object(s) 102, such as a bone or metal plate, may attenuate more of the radiation 120 (e.g., causing fewer photons to impinge upon detector cells underlying the dense aspect than would impinge upon detector cells underlying less dense aspects, such as skin or clothing).

The detector array 106 is configured to directly convert (e.g., using amorphous selenium and/or other direct conversion materials) and/or indirectly convert (e.g., using scintillators and/or other indirect conversion materials) detected radiation into signals that can be transmitted from the detector array 106 to a data acquisition component 122 configured to digitize the signals and/or to generate projection data from the received signals using various techniques (e.g., integration, photon counting, etc.).

The example environment 100 further comprises a projection data generator 124 configured to compile projection data indicative of radiation that impinged the detector within a predetermined time interval, or measurement interval. It may be appreciated that such a measurement interval may be referred to as a "view" and generally reflects signals generated from radiation 120 that was emitted while the radiation source(s) 118 was at a particular angular range relative to the object 102. Typically, the projection data generator 124 is further configured to compile the projection data based upon the radiation energy spectrum of radiation being detected. For example, projection data yielded from the first set of detector cells, configured to detect the first radiation energy spectrum, may be compiled separate from the projection data yielded from the second set of detector cells, configured to detect the second radiation energy spectrum. Thus, within a measurement interval or view, data may be compiled into two (distinct) data sets. A first data set may comprise data indicative of the first radiation energy spectrum (yielded from the first set of detector cells), and a second data set may comprise data indicative of a second radiation energy spectrum (yielded from the second set of detector cells).

In order to generate an image from a data set and/or in order to perform a decomposition process on the data sets, respective data sets typically are required to be complete. That is, data from all or substantially all detector cells of the detector array must be represented in the data set. It may be appreciated that because the first data set generally comprises data merely indicative of the first radiation energy spectrum, data yielded from the second set of detector cells is excluded from the first data set because data yielded from the second set of detector cells is generally indicative of a different radiation energy spectrum. Likewise, data yielded from the first set of detector cells is excluded from the second data set because the second data set is generally indicative of a radiation energy spectrum that differs from the radiation energy spectrum indicated in the data yielded from the first set of detector cells. Thus, as will be describe in more detail below, the projection data generator may be further configured to estimate/approximate the measured data excluded from respective data sets to generate at least two complete data sets (e.g., where a complete first data set is generally indicative of substantially all of the detector cells of the detector array detecting the first energy spectrum (even though data for some of the cells is actually estimated) and a complete second data set is generally indicative of substantially all of the detector cells of the detector array detecting the second energy spectrum (even though data for some of the cells is actually estimated).

The example environment 100 further comprises an image generator 126 configured to receive the complete data sets that are output by the projection data generator 124 and/or data yielded from a decomposition process (e.g., which may be performed by the projection data generator 124). The image generator 126 is also configured to generate image data (also referred to as image(s)) from the complete data sets, which are in projection space, using a suitable analytical, iterative, and/or other image generation technique (e.g., backprojection reconstruction, tomosynthesis reconstruction, iterative reconstruction, etc.). In this way, the data is converted from projection space to image space, a domain that may be more understandable by a user 132 viewing the image(s), for example.

The example environment 100 further comprises a terminal 128, or workstation (e.g., a computer), that may be configured to receive the image data output by the image generator 126. The terminal 128 may also be configured to present the image data and/or information for display on a monitor 130 to a user 132 (e.g., security personnel, medical personnel, etc.). In this way, the user 132 can inspect/review the image(s) to identify areas of interest within the object(s) 102. The terminal 130 can also be configured to receive user input which can direct operations of the object examination apparatus 108 (e.g., a speed to rotate, a speed of a conveyor belt, etc.), for example.

In the example environment 100, a controller 134 is operably coupled to the terminal 128. In one example, the controller 134 is configured to receive input from the terminal 128, such as user input, for example, and to generate instructions for the object examination apparatus 108 indicative of operations to be performed. For example, the user 132 may desire to reexamine the object(s) 102, and the controller 134 may issue a command instructing the support article 112 to reverse direction (e.g., bringing the object(s) 102 back into an examination region 114 of the object examination apparatus 108).

It may be appreciated that the example component diagram is merely intended to illustrate one embodiment of one type of radiation imaging modality and is not intended to be interpreted in a limiting manner. For example, the functions of one or more components described herein may be separated into a plurality of components and/or the functions of two or more components described herein may be consolidated into merely a single component. Moreover, the radiation imaging modality may comprise additional components configured to perform additional features, functions, etc. and/or some components described herein may be optional.

Figure 2:
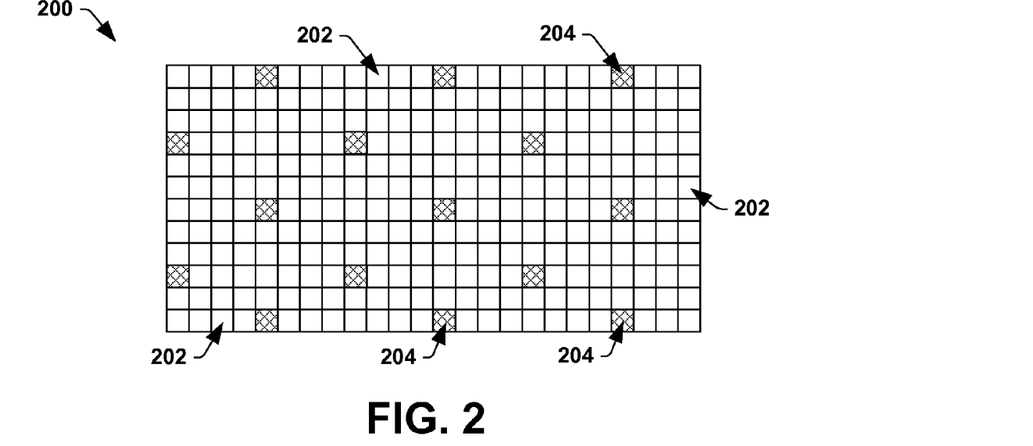
FIG. 2 illustrates a top-down view of an example detector array comprising first and second sets of channels.
Figure 3:
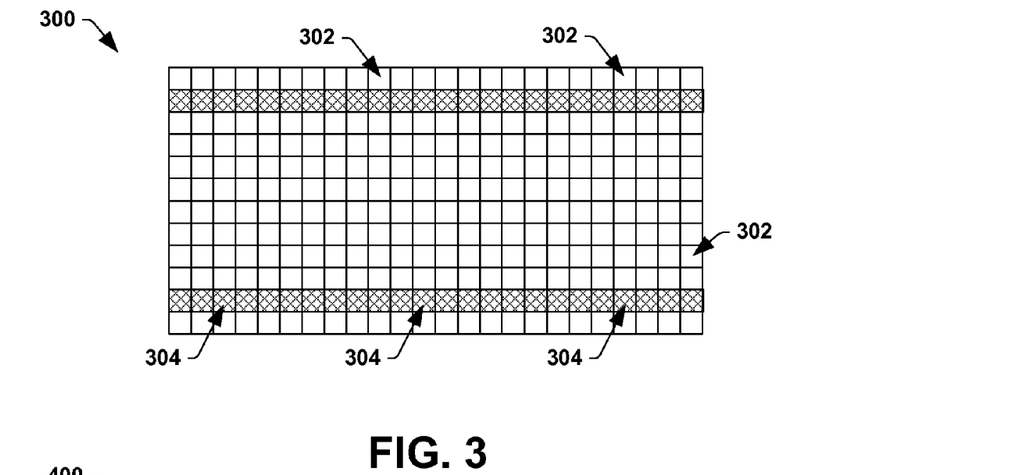
FIG. 3 illustrates a top-down view of an example detector array comprising first and second sets of channels.
Figure 4:
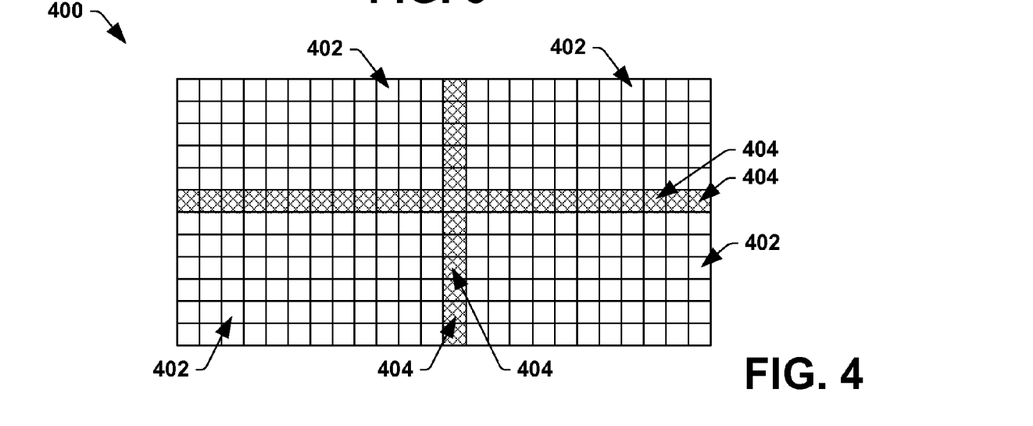
FIG. 4 illustrates a top-down view of an example detector array comprising first and second sets of channels.

As provided herein, the detector array of a radiation imaging modality, such as of a CT system, is comprised of two or more sets of detector cells respectively configured to detect a different radiation energy spectrum. For example, a first set of detector cells may be configured to detect a first radiation energy spectrum and a second set of detector cells may be configured to detect a second radiation energy spectrum. FIGS. 2-4 illustrate top-down views of example detector arrays 200, 300, 400 (e.g., 106 in FIG. 1) respectively illustrating an example arrangement of such detector cells (e.g., looking down at a detection surface upon which radiation impinges (e.g., into the page) and is detected). It may be appreciated that such arrangements are merely example arrangements and are not intended to be construed as limiting the scope of the instant disclosure, including the scope of the claims. It may also be appreciated that, at times, a detector cell(s) may be referred to as a detector channel(s).

FIG. 2 illustrates an example detector array 200 comprising detector cells 202 configured to detect a first radiation energy spectrum (e.g., which together comprise a first set of detector cells) and detector cells 204 (e.g., represented in cross-hatching) configured to detect a second radiation energy spectrum (e.g., which together comprise a second set of detector cells). More particularly, FIG. 2 illustrates an arrangement where the detector cells 204 configured to detect the second radiation energy spectrum are sparsely arranged amongst detector cells 202 configured to detect the first radiation energy spectrum. The ratio of detector cells 202 to detector cells 204 may be application dependent and/or may vary from implementation to implementation (e.g., based upon, among other things, desired image quality). However, in one embodiment, the number of detector cells 202 configured to detect the first radiation energy spectrum relative to detector cells 204 configured to detect the second radiation energy spectrum is typically less than or equal to a 3:1 ratio. Thus, less than 25% of the total detection surface area of the detector array may be occupied by detector cells 204 configured to detect the second radiation energy spectrum, for example.

As described above, the first radiation energy spectrum and the second radiation energy spectrum may be at least partially overlapping. For example, the first radiation energy spectrum (e.g., detectable by the first set of detector cells 202) may span from 80 keV to 100 keV and the second radiation energy spectrum (e.g., detectable by the second set of detector cells 204) may span from 90 keV to 100 keV. In such an embodiment, the second radiation energy spectrum is entirely comprised within the first radiation energy spectrum. In another embodiment, the second radiation energy spectrum may merely partially overlap the first radiation energy spectrum and/or the first and second radiation energy spectra may be non-overlapping. For example, the first radiation energy spectrum may span from 75 keV to 85 keV and the second radiation energy spectrum may span from 90 keV to 100 keV.

Further, the detector array 200 may be configured to differentiate the first energy spectrum from the second energy spectrum (e.g., using the first 202 and second 204 sets of detector cells) when the detector array 200 is manufactured and/or may be later configured to different the first radiation energy spectrum from the second radiation energy spectrum. That is, stated differently, the detector array 200 can be initially configured as a single-energy detector array (e.g., configured to detect merely a single radiation energy spectrum) and may be modified to comprise the first and second sets of detector cells 202, 204 or the detector array 200 can be initially configured as a multi-energy detector array (e.g., configured to detect at least the first and second radiation energy spectra).

By way of example, a filter may be applied to the detector array 200 after the detector array 200 is manufactured. The filter may be configured to attenuate a portion of radiation impinging thereon and may overlay the detection surface of respective cells 204 of the second set, causing the second set of detector cells 204 to detect a different radiation energy spectrum than detector cells 202 of the first set. Such a filter may be configured to attenuate merely a portion of the emitted radiation and may be comprised of metal and/or other partially attenuating materials. For example, in one embodiment, the filter comprises a metallic filter, such as a cooper filter, that is configured to overlay the detection surface of respective cells 204 of the second set. Such a filter may be selectively attached to the detector array 200 or may be permanently affixed to the detector array 200. For example, in one embodiment, the filter comprises an adhesive material (e.g., such as an adhesive tape, etc.) that is applied to the detection surface of the respective detector cells 204. In such an embodiment, the detector cells 204 of the second set may be reconfigured at a later time by replacing the adhesive material with new adhesive material configured to filter (e.g., attenuate) a different radiation energy spectrum, for example.

In another embodiment, the detector cells 204 of the second set may be configured, at the time of manufacturing, to detect a different radiation energy spectrum than the detector cells 202 of the first set. For example, a thicker scintillator material and/or a different type of scintillator material may be applied to the detector cells 204 relative to the thickness and/or type of scintillator material applied to the detector cells 202 of the first set.

It may be appreciated that although continued reference is made to applying a filter to detector cells 204 of the second set and/or manufacturing the detector cells 204 with a thicker scintillator material (e.g., causing a higher radiation energy spectrum to be detected by the detector cells 204 of the second set relative to the spectrum detected by the detector cells 202), a filter may be applied to the detector cells 202 of the first set and/or the detector cells 202 may be manufactured with the thicker scintillator material, for example. Thus, the detector cells 202 may be configured to detect a higher energy spectrum than the detector cells 204 and/or vice-versa. Further, both sets of detector cells 202, 204 may comprise a filter, with a filter applied to one set of detector cells being different than a filter applied to another set of detector cells, for example.

FIG. 3 illustrates yet another example detector array 300 comprising detector cells 302 configured to detect a first radiation energy spectrum (e.g., which together comprise a first set of detector cells) and detector cells 304 (e.g., represented in cross-hatching) configured to detect a second radiation energy spectrum (e.g., which together comprise a second set of detector cells). More particularly, FIG. 3 illustrates an arrangement where the detector cells 304, configured to detect the second radiation energy spectrum, comprise two rows of the detector array 300 and the remaining rows are comprised of detector cells 302 configured to detect the first radiation energy spectrum. Although the example arrangement illustrates the detector cells 304 as comprising two rows, it may be appreciated that detector cells 304 of the second set may be arranged to form more or fewer than two rows. Moreover, such detector cells 304 may be arranged to form one or more partial rows, for example.

FIG. 4 illustrates yet another example detector array 400 comprising detector cells 402 configured to detect a first radiation energy spectrum (e.g., which together comprise a first set of detector cells) and detector cells 404 (e.g., represented in cross-hatching) configured to detect a second radiation energy spectrum (e.g., which together comprise a second set of detector cells). More particularly, FIG. 4 illustrates an arrangement where the detector cells 404, configured to detect the second radiation energy spectrum, are arranged to form a row and a column in the detector array 400. Remaining rows and columns of detector array 400 comprise detector channels 402 configured to detect the first radiation energy spectrum. Again, although the example arrangement illustrates the detector cells 404 as being arranged to form a single column and a single row, it may be appreciated that detector cells 404 of the second set may be arranged to form more than one column and/or more than one row. Moreover, such detector cells 404 may be arranged to form one or more partial columns and/or one or more partial rows, for example.

Figure 5:
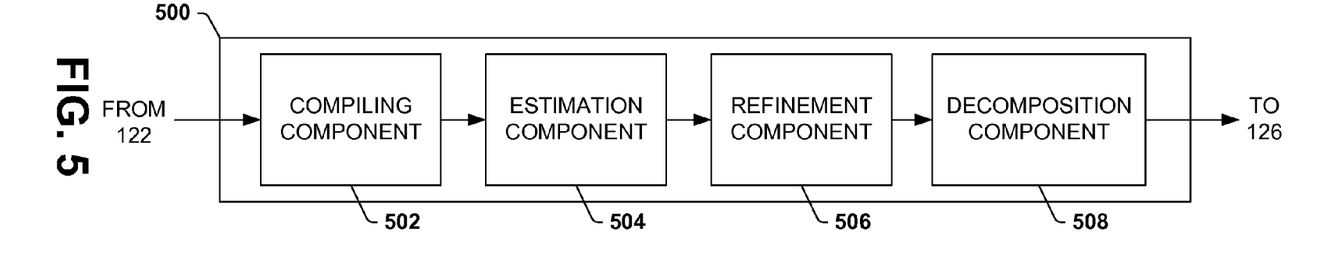
FIG. 5 illustrates an example system for generating multi-energy projection data.

FIG. 5 is a component block diagram illustrating an example system configured to yield multi-energy data that may be utilized by an image reconstructor (e.g., 126 in FIG. 1) to generate one or more images indicative of density and/or atomic number (e.g., z-effective) characteristics of an object undergoing or that underwent an examination by a radiation imaging modality. More particularly, FIG. 5 is a component block diagram illustrating an example projection data generator 500 (e.g., 124 in FIG. 1) configured to yield multi-energy data, which may be further processed to generate one or more multi-energy images, for example.

The projection data generator 500 comprises a compiling component 502, an estimation component 504, a refinement component 506, and a decomposition component 508. It may be appreciated that although FIG. 5 illustrates such components as being comprised within a projection data generator 500, one or more of the components may be located outside the projection data generator 500. Moreover, one or more functions described as being performed by two or more components may be performed by a single component and/or the functions of a component may be divided into two or more components. Further, it may be appreciated that while the following description provides for the functions carried out for data representing a single measurement interval, or view, such functions may be repeated for multiple views if so desired.

The compiling component 502 is configured to generate two or more partial data sets from measured data acquired from a data acquisition component (e.g., 122 in FIG. 1), where the data is divided into data sets based upon the radiation energy spectrum of the detector cell from which the data is yielded. By way of example, in one embodiment, the compiling component 502 may be configured to compile measured data yielded from a first set of detector cells (e.g., 202 in FIG. 2), configured to detect a first radiation energy spectrum, to generate a partial first data set indicative of the first radiation energy spectrum. Similarly, the compiling component 502 may be configured to compile measured data yielded from a second set of detector cells (e.g., 204 in FIG. 2), configured to detect a second radiation energy spectrum, to generate a partial second data set indicative of the second radiation energy spectrum. It may be appreciated that the compiling component 502 may be configured to exclude, from the partial first data set, all or substantially all measured data yielded from the second set of detector cells because first partial data set is generally indicative of the first energy spectrum and the second set of detectors is generally configured to yield data indicative of the second energy spectrum. Likewise, the compiling component 502 may be configured to exclude, from the partial second data set, all or substantially all measured data yielded from the first set of detector cells because the second partial data set is generally indicative of the second energy spectrum and the first set of detector cells is generally configured to yield data indicative of the first energy spectrum.

The estimation component 504 is configured to estimate data excluded from respective partial data sets to generate complete data sets. That is, a complete data set typically comprises data yielded from all or substantially all of the detector cells of a detector array. Because the measured data yielded from the second set of detector cells is excluded from the first set of data and because the measure data yielded from the first set of detector cells is excluded from the second set of data, neither the partial first data set nor the partial second data set is a complete set. As such, the estimation component 502 may be configured to estimate the data excluded from the partial first data set and to estimate the data excluded from the partial second data set. That is, stated differently, the estimation component 504 is configured to estimate, for the first data set, data that would have been produced by the second set of detector cells had the second set of detector cells been configured to detect the first radiation energy spectrum (e.g., referred to as an estimated first data set). In this way, using the measured data from the first set of detector cells (e.g., the partial first data set) and the estimate for data that would have been produced by the second set of detector cells (e.g., the estimated first data set), the estimation component 502 may be configured to generate a complete first data set indicative of the first radiation energy spectrum (e.g., as if all or substantially all detector cells of the detector array detected the first radiation energy spectrum). Likewise, the estimation component 504 is configured to estimate, for the second data set, data that would have been produced by the first set of detector cells had the first set of detector cells been configured to detect the second radiation energy spectrum (e.g., referred to as an estimated second data set). Using the measured data from the second set of detector cells (e.g., the partial second data set) and the estimate for data that would have been produced by the first set of detector cells (e.g., the estimated second data set), the estimation component 502 may be configured to generate a complete second data set indicative of the second radiation energy spectrum (e.g., as if all or substantially all detector cells of the detector array detected the second radiation energy spectrum).

Techniques utilized to derive the estimated first data set may be different than the techniques utilized to derive the estimated second data set. For example, in one embodiment, the amount of measured data indicative of the second radiation energy spectrum is (substantially) less than the amount of measured data indicative of the first radiation energy spectrum (e.g., because a greater number of cells are detecting the first radiation energy spectrum as illustrated in FIGS. 2-4). By way of example, in one embodiment, given the amount of measured data indicative of the first radiation energy spectrum, the estimation component 504 may be configured to interpolate (e.g., using standard interpolation techniques such as those utilized when a detector cell is malfunctioning) the measured data indicative of the first radiation energy spectrum to estimate the data that would have been yielded by the second set of cells. Thus, the estimation component 504 may be configured to derive the estimated first data set merely from the measured data indicative of the first radiation energy spectrum.

It may be appreciated that such a technique may or may not be utilized to derive the estimated second data set because less data is available from which such an interpolation may be performed (e.g., because fewer detector cells comprise the second set of detector cells). As such, in one embodiment, the estimation component 504 may be configured to derive the estimated second data set using both the measured data from the second set of cells and the complete first data set. In this way, data indicative of the first energy spectrum and data indicative of the second energy spectrum may be utilized to generate the estimated second data set, and thus the complete second data set, indicative of the second radiation energy spectrum. That is, stated differently, when the amount of measured data indicative of the second radiation energy spectrum is (substantially) less than the amount of measured data indicative of the first radiation energy spectrum the estimation of the second data set is inherently an ill-posed problem. To stabilize an ill-posed estimation problem, it may be necessary to adopt one or more regularization approaches. As an example, in one embodiment, the estimation component 504 may be configured to apply an edge-preserving regularization method to the measured data indicative of the second energy spectrum and the complete first data set indicative of the first energy spectrum to derive/generate the estimated second data set, or rather the estimated portion of the complete second data set.

The projection data generator 500 further comprises a refinement component 506 configured to refine the complete second data set or the estimated portion of the complete second data set by comparing the complete first data set to the complete second data set. As an example, given that the complete first and second data sets are intended to represent a same view of the object at different energy spectrums, a distribution of intensities (e.g., when intensities are plotted relative to detector cells as show in FIG. 11) between the complete first data set and the complete second data set should be substantially similar but should differ in magnitude. Thus, the refinement component 506 may compare intensities of the complete first data set against intensities of the complete second data set (e.g., using an axial gradient) to determine whether the intensities vary merely in magnitude or also in shape. Where the intensities differ in shape, the refinement component 506 may be configured to iteratively refine estimates made to generate the complete second data set, or to the estimated portion of the complete second data set, until a distribution of intensities represented by the complete second data set substantially matches, in shape, a distribution of intensities represented by the first complete data set and/or until other stopping criteria has been met.

The projection data generator 500 further comprises a decomposition component 508 configured to decompose attenuation coefficients, for example, of respective complete data sets using analytic, iterative, and/or other multi-energy (dual-energy) decomposition techniques. Because the complete first data set is indicative of a different energy spectrum than the complete second data set, attenuation coefficients may be different even though the data is representative of the same object and the same view, for example, allowing z-effective information and density information, for example, to be derived from the examination. The decomposed, or multi-energy, data output by the decomposition component may be transmitted to an image generator (e.g., 126 in FIG. 1), where the multi-energy data may be converted from projection space to image space to produce one or more multi-energy images, for example.

Figure 6:
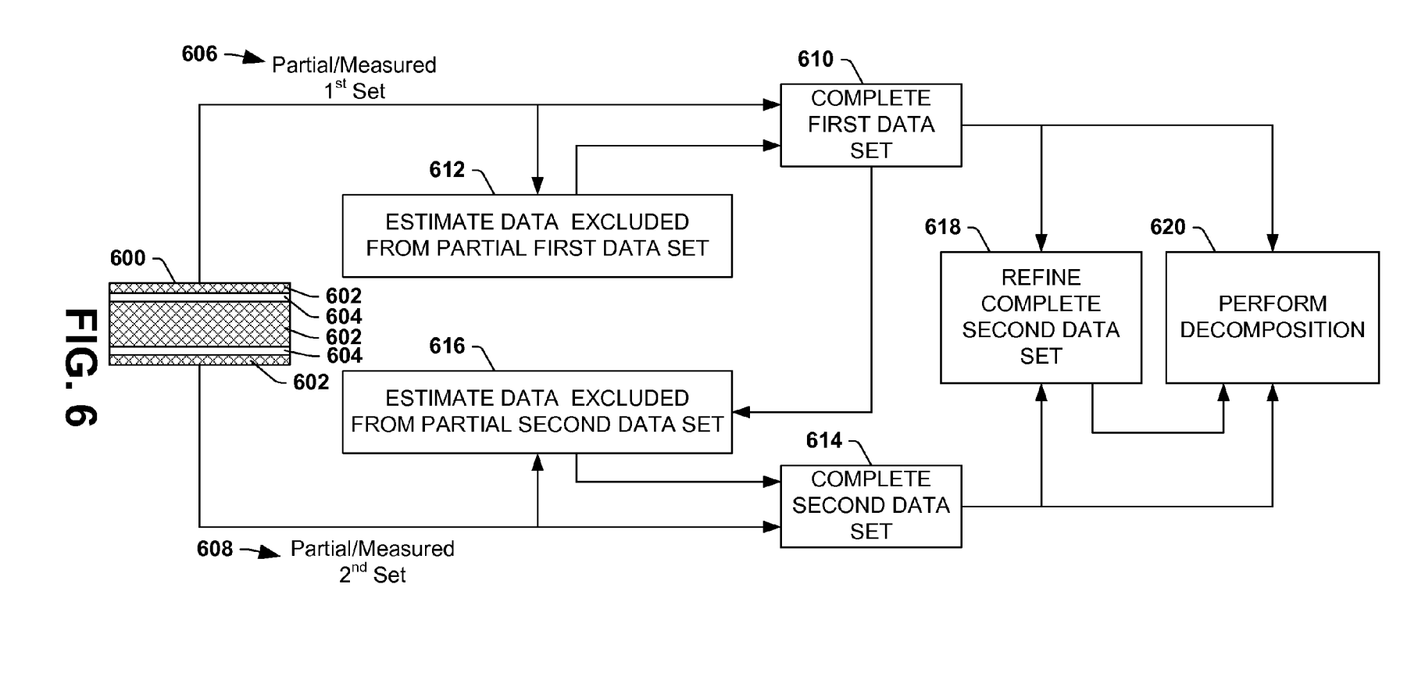
FIG. 6 illustrates an example flow diagram for generating multi-energy projection data.

FIG. 6 illustrates an example flow diagram for generating two complete data sets, respectively indicative of a different radiation energy spectrum and for decomposing the two complete data sets to generate multi-energy projection data from which multi-energy images may be generated, for example.

A detector array 600 (e.g., 300 in FIG. 3) is comprised of a plurality of detector cells divided into two sets 602, 604, respectively configured to detect a different energy spectra and to output data indicative of the detected energy spectra. For example, the cross-hatched portion of the detector array 600 may represent a first set 602 of detector cells and the portion that is not cross-hatched may represent a second set 604 of detector cells. Data output by the first set 602 of detector cells may be compiled by a compiling component (e.g., 502 in FIG. 5) to generate a partial first data set 606 indicative of the first radiation energy spectrum (e.g., also referred to as a measured first data set because the data set is representative of detected radiation) and a partial second data set 608 indicative of the second radiation energy spectrum (e.g., also referred to as a measured second set). It may be appreciated that the partial first and second data sets are typically representative of a same, or substantially, same view of the object.

To generate a complete first data set 610, indicative of the first radiation energy spectrum and representative of information from all or substantially all of the detector cells (e.g., as opposed to merely the cross-hatched portion of the detector array), an estimation component (e.g., 504 in FIG. 5) uses the partial/measured first data set 606 to estimate 612 data that would have been produced by the second set of detector cells if the second set of detector cells had been configured to detect the first radiation energy spectrum (e.g. where the estimated data may be referred to as an estimated first data set). Thus, a complete first data set is generated based upon the partial/measured first data set, indicative of the first radiation energy spectrum, and estimated first data set, also indicative of the first radiation energy.

The generate a complete second data set 614, indicative of the second radiation energy spectrum and representative of information from all or substantially all of the detector cells, the estimation component (e.g., 504 in FIG. 5) uses the partial/measured second data set 608 to estimate 616 data that would have been produced by the first set of detector cells if the first set of detector cells had been configured to detect the second radiation energy spectrum (e.g. where the estimated data may be referred to as an estimated second data set). However, because of the limited amount of data that comprises the partial/measured second data set 608 (e.g., because merely two rows of detector cells 604 are configured to yield such data), the partial/measured second data set 608 may be insufficient to estimate data indicative of the second radiation energy spectrum. As such, the complete first data set 610 may also be utilized when estimating 616 data indicative of the second radiation energy spectrum that would have been produced by the first set of detector cells if configured to detect the second radiation energy spectrum. Thus, a complete second data set 614 is generated based upon the partial/measured second data set 608, indicative of the second radiation energy, and the complete first data set 610, indicative of the first radiation energy. By way of example, an edge-preserving regularization algorithm may be applied to generate the estimated second data set (e.g., which is used to establish the complete second data set 614) based upon the partial/measured second data set 608 and the complete first data set 610.

To refine 618 the complete second data set (e.g., which may be predominately comprised of estimated data as opposed to measured data), the complete first data set 610 may be compared to the complete second data set 614 (e.g., by the refinement component 506 of FIG. 5) using an analytic, iterative, and/or other projection data refinement techniques configured to refine the data comprised in the complete second data set 614 (or refine the estimates). By way of example, in one embodiment, the complete second data set 614 is utilized to generate an expected first data set that is expected to have been produced if the estimates comprised in the complete second data 614 are accurate. The expected first data set may then be compared to the complete first data set 610, and based upon differences between the expected first data set and the complete first data set 610, the complete second data set 614 (or an estimated portion of the complete second data set 614) may be refined, for example.

A multi-energy decomposition process 620 may then be performed on the complete first data set and the completed/refined second data set by a decomposition component (e.g., 508 in FIG. 5) to derive basic components of the object (e.g., density and/or atomic number), for example.

FIGS. 7-11 illustrate example distributions 700, 800, 900, 1000, 1100, 1102 plotting intensities measured by respective detector cells during a measurement interval throughout the process described with respect to FIG. 6. The y-axis 702 represents an intensity value and the x-axis 704 represents the detector cell measuring the intensity. That is, stated differently, respective detector cells of a detector array are assigned a numerical reference number and are arranged on the x-axis according to the reference number. That, a first detector cell may be represented at a first location on the x-axis and a second detector cell may be located at a second location on the x-axis, with the intensity measured by respective detector cells (during a view or measurement interval) being represented by the y-value of the distribution.

Figure 7:
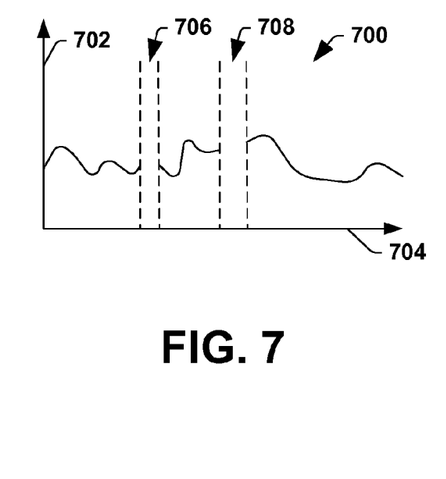
FIG. 7 illustrates an example distribution of data yielded from a first set of detector cells indicative of a first radiation energy spectrum.

FIG. 7 illustrates an example distribution 700 of intensities represented in a partial/measured first data set (e.g., 606 of FIG. 6) yielded from a first set of detector cells, configured to detect a first radiation energy spectrum. As previously described, the partial first data set excludes data yielded from a second set of detector cells, configured to detect a second radiation energy spectrum, because the second set of detector cells are measuring a different radiation energy spectrum than the first set of detector cells. As such, the first partial/measured first data set may be considered incomplete. That is, data from detector cells configured to detect the second radiation energy spectrum (e.g., where such detector cells may be defined as detector cells within the portions 706, 708 of the distribution 700) is not included in the partial/measured first data set causing the distribution to be discontinuous, for example.

Figure 8:
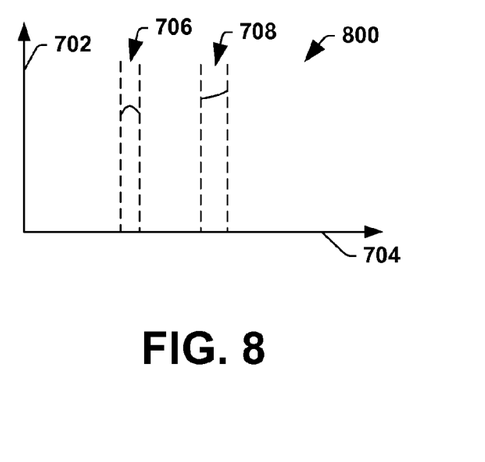
FIG. 8 illustrates an example distribution of data yielded from a second set of detector cells indicative of a second radiation energy spectrum.

FIG. 8 illustrates an example distribution 800 of intensities represented in a partial/measured second data set (e.g., 608 of FIG. 6) yielded from a second set of detector cells (e.g., where such detector cells may be defined as detector cells within the portions 706, 708 of the distribution 800), configured to detect a second radiation energy spectrum. As previously described, the partial second data set excludes data yielded from a first set of detector cells, configured to detect a first radiation energy spectrum, because the first set of detector cells are measuring a different radiation energy spectrum than the second set of detector cells. As such, the second partial/measured data set may be considered incomplete. That is, data from detector cells configured to detect the first radiation energy spectrum (e.g., which are represented in the example distribution 700 of FIG. 7) is not included in the partial/measured second data set. It may be appreciated that if the distributions 700 and 800 represented in FIGS. 7 and 8, respectively, were combined, substantially all of the data yielded from a detector array during a measurement interval may be represented in the combined distribution.

Figure 9:
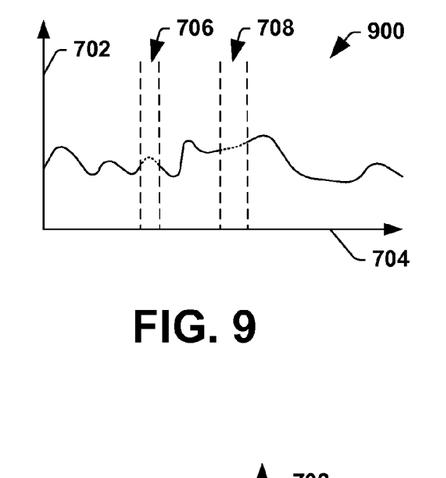
FIG. 9 illustrates an example distribution of a complete first data set indicative of a first radiation energy spectrum.

FIG. 9 illustrates an example distribution 900 of intensities for a complete first data set (e.g., 610 in FIG. 6) (e.g., after an estimated first data set has been derived/generated and combined with the partial first data set). The estimated portion of the complete first data set is indicative of data that would have been measured by a second set of detector cells (e.g., where such detector cells may be defined as detector cells within the portions 706, 708 of the distribution 900) and is represented by dashed lines. The solid lines represent the partial/measured first data set. Given the small amount of data excluded from the partial first data set, it may be appreciated that such an estimate may be performed by interpolating the partial/measured first data set, which is represented in the distribution 700 of FIG. 7.

Figure 10:
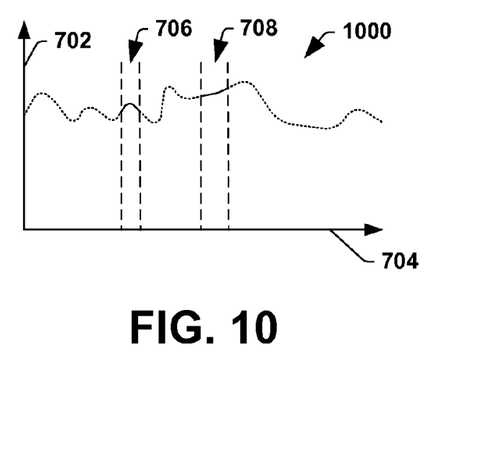
FIG. 10 illustrates an example distribution of a complete second data set indicative of a second radiation energy spectrum.

FIG. 10 illustrates an example distribution 1000 of intensities for a complete second data set (e.g., 614 in FIG. 6) (e.g., after an estimated second data set has been derived/generated and combined with the partial second data set). The estimated portion of the complete second data set is indicative of data that would have been measured by a first set of detector cells and is represented by dashed lines. The solid lines represent the partial/measured second data set yielded from the second set of detector cells (e.g., where such detector cells may be defined as detector cells within the portions 706, 708 of the distribution 1000). It may be appreciated that given the significant amount of data that is to be estimated relative to the amount of partial/measured data indicative of the second energy spectrum, an estimation for the excluded detector cells may not be feasible using merely the partial/measured data indicative of the second energy spectrum. As such, the complete first data set (e.g., as illustrated in the distribution 900 of FIG. 9) and the partial/measured data indicative of the second energy spectrum (e.g., as illustrated in the distribution 800 of FIG. 8) may be utilized to generate/derive the complete second set of data as illustrated via the distribution 1000 in FIG. 10.

Figure 11:
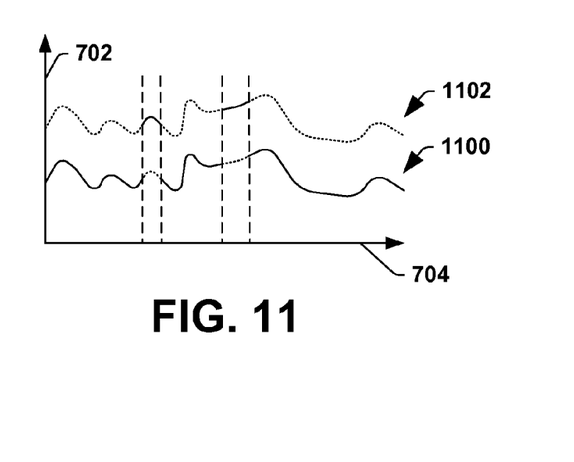
FIG. 11 illustrates example distributions of complete first and second data sets respectively indicative of a first and second radiation energy spectrum.

As illustrated in FIG. 11, the distribution 1100 of intensities associated with the complete first data set should be substantially similar in shape to the distribution 1102 of intensity values associated with the complete second data set but different in magnitude (e.g., given that the complete first and second data sets are representative of a substantially similar view of an object). Based upon this principle, for example, the complete first data set may be compared to the complete second data set to iteratively refine the estimates comprised in the complete second data set until a stopping criteria is met, for example. In this way, two complete data sets, respectively representative of a different radiation energy spectrum may be generated from the two partial/measured data sets, but where merely a single detector array is utilized, for example.

Figure 12:
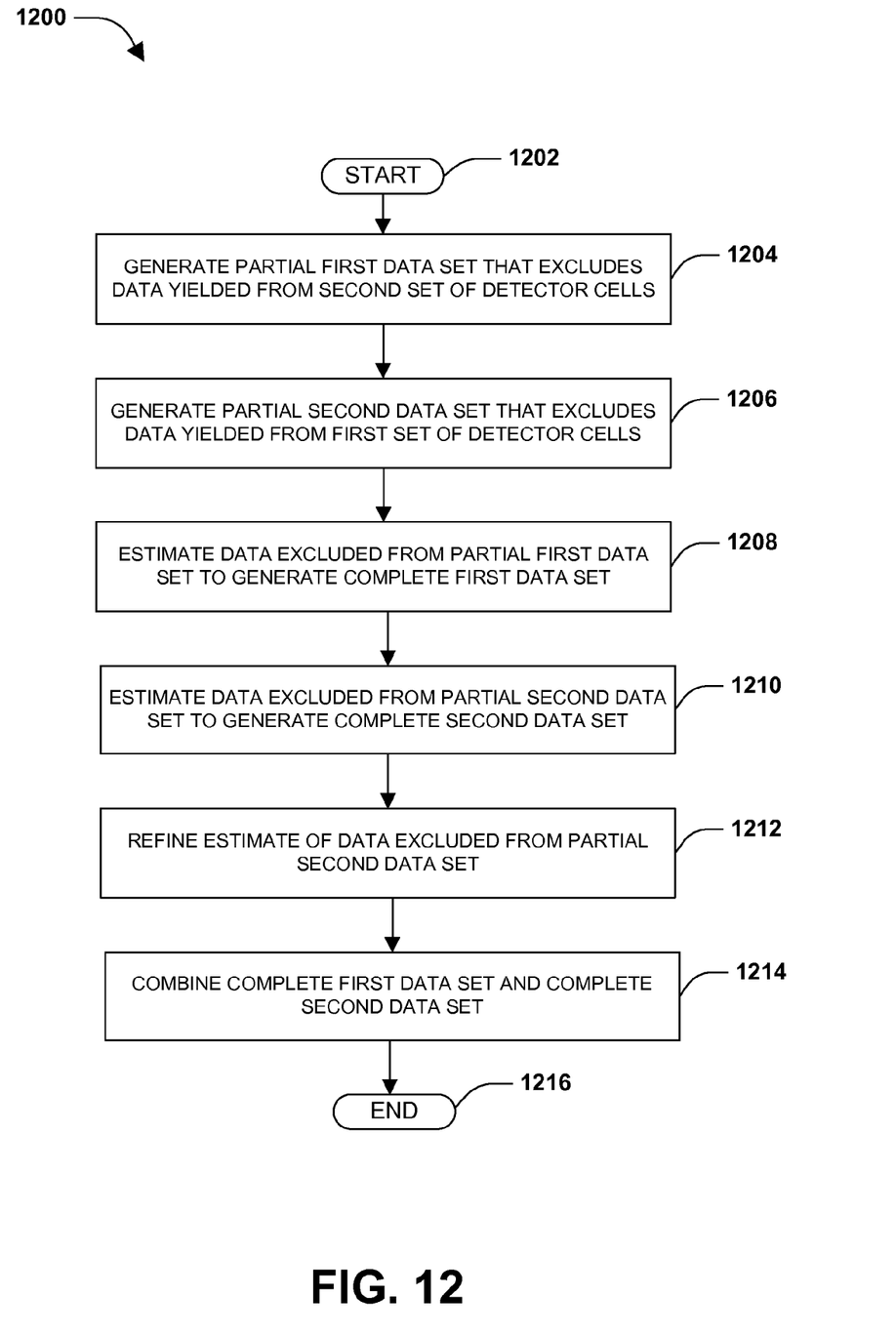
FIG. 12 is a flow diagram illustrating an example method for generating multi-energy data.

FIG. 12 illustrates an example method 1200 for estimating multi-energy projection data comprising data indicative of a first radiation energy spectrum and data indicative of a second radiation energy spectrum, using a radiation imaging modality. A first set of detector cells (e.g., 202 in FIG. 2) of a detector array is configured to detect the first radiation spectrum and a second set of detector cells (e.g., 204 in FIG. 2) of the detector array is configured to detect the second radiation spectrum. It may be appreciated that, to the extent practical, the arrangement/order of the acts illustrated in FIG. 12 and described herein provide merely an example arrangement/order as some acts may be performed concurrently and/or some acts may be independent of other acts described herein.

The example method 1200 begins at 1202, and a partial first data set is generated at 1204. The partial first data set, which is indicative of the first radiation energy spectrum, comprises measured data yielded from the first set of detector cells during a measurement interval, or view. That is, stated differently, during an examination of an object via radiation, an object and an underlying detector array are exposed to radiation. Radiation that impinges the underlying detector array or rather detector cells of the underlying detector array is converted into analog signals and ultimately into projection data. Projection data yielded from the first set of detector cells is assembled or compiled to generate the partial first data set (e.g., which is still in a projection space domain).

Projection data yielded from the second set of detector cells is not comprised within this partial first data set because the measured data yielded from the second set of detector cells is representative of the second energy spectrum, which is different than the first energy spectrum. Thus, measured data yielded from the second set of detector cells is excluded from the partial first data set, which is indicative of the first radiation energy spectrum.

At 1206 in the example method 1200, a partial second data set is generated. The partial second data set, which is indicative of the second radiation energy spectrum, comprises measured data yielded from the second set of detector cells during the measurement interval. That is, measured data yielded from the second set of detector cells is assembled or compiled to generate the partial second data set (e.g., which is also still in a projection space domain). Projection data yielded from the first set of detector cells is not comprised within the partial second data set because the measured data yielded from the first set of detector cells is representative of the first energy spectrum. Thus, measured data yielded from the first set of detector cells is excluded from the partial second data set, which is indicative of the second radiation energy spectrum.

At 1208 in the example method 1200, the data excluded from the partial first data set is estimated. That is, projection data that would have been yielded from the second set of detector cells if the cells had been configured to detect the first radiation energy spectrum (e.g., as opposed to the second radiation energy spectrum) is estimated and combined with the partial first data set to generate a complete first data set indicative of the first energy spectrum. Such estimated data may be referred to as an estimated first data set because it is related to the first data set (e.g., indicative of a same view and same radiation spectrum) and used, in conjunction with the partial or measured first data set, to generate the complete first data set (e.g., where the complete first data set comprises a combination of the estimated first data set and the partial first data set).

The estimation may be based upon the partial first data set. That is, the measured data indicative of the first energy spectrum may be utilized to derive estimated data indicative of the first energy spectrum. For example, analytic, iterative, and/or other estimation techniques (e.g., such as interpolation techniques commonly used to estimate data for a defective detector cell) may be utilized to derive the estimated data using the partial first data set.

At 1210 in the example method 100, the data excluded from the partial second data set is estimated. That is, projection data that would have been yielded from the first set of detector cells if the cells had been configured to detect the second radiation energy spectrum (e.g., as opposed to the first radiation energy spectrum) is estimated and combined with the second partial data set to generate a complete second data set indicative of the second radiation energy spectrum. It may be appreciated that the estimated data may be referred to as an estimated second data set because it is related to the second data set (e.g., indicative of a same view and same radiation spectrum) and used, in conjunction with the partial or measured second data set to generate the complete second data set (e.g., where the complete second data set comprises a combination of the estimated second data set and the partial second data set).

As described with respect to FIGS. 2-5, the amount of data comprised in the partial second data set may be insufficient to estimate the estimated second data set. That is, stated differently, the partial second data set may not comprise enough data references from which to perform an interpolation to derive the estimated second data set. As such, as further described in FIGS. 5-6, the estimated second data set may be derived using the complete first data set (e.g., indicative of the first energy spectrum) and using the partial second data (e.g., indicative of the second energy spectrum). For example, in one embodiment, estimating the data excluded from the partial second data set may comprise using an edge-preserving technique that is configured to utilize both the complete first dataset and the partial second data set to generate the estimated second data set.

At 1212 in the example method 1200, the estimate of the data excluded from the partial second data set (e.g., the estimated second data set generated at 1210) is refined to improve the accuracy of the estimation, for example. By way of example, the first complete data set may be compared to the second complete data set by mapping the estimated data excluded from the partial first data set (e.g., the estimated first data set) to the partial second data set. The estimate of the data excluded from the partial second data set may then be updated according to the mapping based upon an axial gradient of the partial first data set, for example. In one embodiment, such a refinement may be iteratively repeated until one or more stopping criteria is meet, at which point the present iteration of the complete second data set may be output to a decomposition component (e.g., 508 in FIG. 5), for example.

At 1214 in the example method 1200, the complete first data set and the present iteration of the complete second data set are combined. For example, in one embodiment, a multi-energy decomposition algorithm may utilize the complete first and second data sets to decompose the data sets and identify features of the examined object, such as density characteristics and/or atomic number characteristics of the object. In this way, one or more images representative of density and/or atomic number characteristics may be generated for example. That is, via the decomposition algorithm, multi-energy projection data may be generated from which multi-energy images may be generated.

The example method 1200 ends at 1216.

Figure 13:
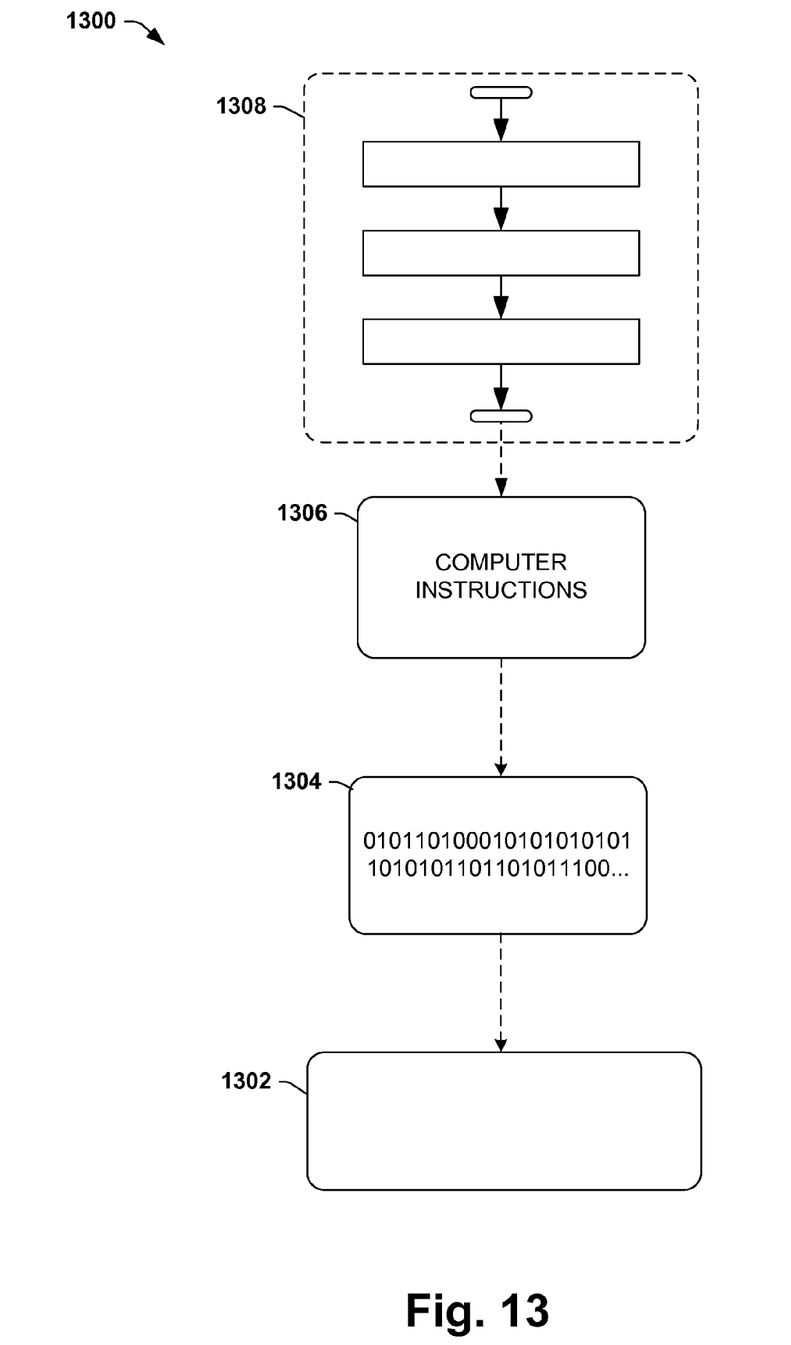
FIG. 13 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 13, wherein the implementation 1300 comprises a computer-readable medium 1302 (e.g., a CD-R, DVD-R, or a platter of a hard disk drive), on which is encoded computer-readable data 1304. This computer-readable data 1304 in turn comprises a set of computer instructions 1306 configured to operate according to one or more of the principles set forth herein. In one such embodiment 1300, the processor-executable instructions 1306 may be configured to perform a method 1308, such as at least some of the example method 1200 of FIG. 12, for example. In another such embodiment, the processor-executable instructions 1306 may be configured to implement a system, such as at least some of the exemplary environment 100 of FIG. 1 and/or exemplary system 500 of FIG. 5, for example. Many such computer-readable media may be devised by those of ordinary skill in the art that are configured to operate in accordance with one or more of the techniques presented herein.

Moreover, the words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications may occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A method to estimate multi-energy data, comprising data indicative of a first radiation energy spectrum and data indicative of a second radiation energy spectrum, in a radiation imaging modality comprising a detector array comprised of a plurality of detector cells, a first set of the detector cells configured to detect the first radiation energy spectrum and a second set of the detector cells configured to detect the second radiation energy spectrum, the method comprising:
generating a partial first data set using data yielded from the first set of detector cells, the partial first data set excluding data yielded from the second set of detector cells;
generating a partial second data set using data yielded from the second set of detector cells, the partial second data set excluding data yielded from the first set of detector cells;
estimating the data excluded from the partial first data set based upon the partial first data set to generate a complete first data set indicative of the first radiation energy spectrum; and
estimating the data excluded from the partial second data set based upon the partial second data set and the complete first data set to generate a complete second data set indicative of the second radiation energy spectrum.

2. The method of claim 1, estimating the data excluded from the partial second data set comprising using an edge-preserving regularization algorithm.

3. The method of claim 1, estimating the data excluded from the partial first data set comprising performing interpolation using the partial first data set.

4. The method of claim 1, comprising refining the estimate of the data excluded from the partial second data set using the complete second data set and the complete first data set.

5. The method of claim 1, comprising refining the estimate of the data excluded from the partial second data set, comprising:
mapping the estimate of the data excluded from the partial first data set to the partial second data set; and
updating the estimate of the data excluded from the partial second data set based upon the mapping.

6. The method of claim 1, comprising combining the complete first data set and the complete second data set to generate one or more images representative of density and atomic number characteristics of an object examined by the radiation imaging modality.

7. The method of claim 6, combining the complete first data set and the complete second data set comprising using a multi-energy decomposition algorithm.

8. The method of claim 1, wherein:
generating the partial first data set comprises generating the partial first data set in projection space, and
generating the partial second data set comprises generating the partial second data set in projection space.

9. The method of claim 1, wherein the complete first data set and the complete second data set are in a projection space domain.

10. The method of claim 1, the radiation imaging modality comprising a computed tomography (CT) system.

11. The method of claim 1, the second set of detector cells comprising a filter and the method comprising filtering at least a portion of radiation impinging the second set of detector cells such that the second set of detector cells merely detects radiation with an energy within the second radiation energy spectrum.

12. The method of claim 11, the filter comprising an adhesive material configured to be adhered to a detection surface of respective detector cells comprised within the second set of detector cells.

13. A multi-energy radiation imaging system, comprising:
a radiation source configured to emit radiation;
a detector array comprising a plurality of detector cells, a first set of detector cells configured to detect a first radiation energy spectrum of emitted radiation and a second set of detector cells configured to detect a second radiation energy spectrum of emitted radiation;
a compiling component configured to:
generate a partial first data set using data yielded from the first set of detector cells, the partial first data set excluding data yielded from the second set of detector cells, and
generate a partial second data set using data yielded from the second set of detector cells, the partial second data set excluding data yielded from the first set of detector cells; and
an estimation component configured to:
estimate the data excluded from the partial first data set based upon the partial first data set to generate a complete first data set indicative of the first radiation energy spectrum, and
estimate the data excluded from the partial second data set based upon the partial second data set and the complete first data set to generate a complete second data set indicative of the second radiation energy spectrum.

14. The system of claim 13, comprising a refinement component configured to refine the estimate of the data excluded from the partial second data set by comparing the complete second data set to the complete first data set.

15. The system of claim 13, comprising an image generator configured to generate one or more images indicative of density and atomic number using the complete first data set and the complete second data set.

16. The system of claim 13, comprising a decomposition component configured to utilize a multi-energy decomposition algorithm to combine the complete first data set and the complete second data set to yielded multi-energy data.

17. The system of claim 13, the estimation component configured to estimate the data excluded from the partial second data set using an edge-preserving regularization algorithm.

18. The system of claim 13, the second set of detector cells comprising a filter, the filter configured to filter a portion of the emitted radiation such that merely the radiation having an energy within the second radiation energy spectrum passes through the filter.

19. The system of claim 18, the filter comprising an attachable member configured to be selectively attached to detector cells of the second set of detector cells.

20. A computer readable medium comprising computer executable instructions that when executed via a processing unit perform a method to estimate multi-energy data, comprising data indicative of a first radiation energy spectrum and data indicative of a second radiation energy spectrum, in a radiation imaging modality comprising a detector array comprised of a plurality of detector cells, a first set of the detector cells configured to detect the first radiation energy spectrum and a second set of the detector cells configured to detect the second radiation energy spectrum, the method comprising:

generating a partial first data set using data yielded from the first set of detector cells, the partial first data set excluding data yielded from the second set of detector cells;

generating a partial second data set using data yielded from the second set of detector cells, the partial second data set excluding data yielded from the first set of detector cells;

estimating the data excluded from the partial first data set based upon the partial first data set to generate a complete first data set indicative of the first radiation energy spectrum; and estimating the data excluded from the partial second data set based upon the partial second data set and the complete first data set to generate a complete second data set indicative of the second radiation energy spectrum.

* * * * *